United States Patent [19]

Doll

[11] 4,036,215
[45] July 19, 1977

[54] APPARATUS AND METHOD FOR ELIMINATING PERTURBATIONS OF A KINETIC ORIGIN IN THE BLOOD FLOW WAVEFORM

[75] Inventor: Henri Georges Doll, New York, N.Y.

[73] Assignee: Doll Research, Inc., New York, N.Y.

[21] Appl. No.: 547,630

[22] Filed: Feb. 6, 1975

[51] Int. Cl.$^2$ .............................................. A61B 5/02
[52] U.S. Cl. ........................... 128/2.05 F; 73/194 EM
[58] Field of Search ...................... 128/2.05 F, 2.05 B, 128/2.05 V; 73/194 EM

[56] References Cited

U.S. PATENT DOCUMENTS

| | | | |
|---|---|---|---|
| 2,929,247 | 3/1960 | Sturgeon | 73/194 EM |
| 3,377,855 | 4/1968 | Coia et al. | 73/194 EM |
| 3,449,951 | 6/1969 | Westersten | 73/194 EM |
| 3,659,591 | 5/1972 | Doll et al. | 128/2.05 F |
| 3,717,031 | 2/1973 | Biscar | 73/194 EM |
| 3,757,773 | 9/1973 | Kolin | 128/2.05 F |
| 3,863,172 | 1/1975 | Sato et al. | 73/194 EM |

Primary Examiner—Kyle L. Howell
Attorney, Agent, or Firm—Kenyon & Kenyon Reilly, Carr & Chapin

[57] ABSTRACT

A measuring technique for eliminating the ballistic artifacts created by the mechanical body recoil upon the motion of the heart and the surge of blood within each heart cycle. The limb is restrained by mechanical devices which channel the kinetic energy into a motion which is in a plane favorable to the measurement. A magnetic field is created in the area where blood flow is to be recorded. The ballistic artifact creates a perturbative component in the desired blood flow waveform recording. This perturbation is eliminated by placing an electrically conductive loop around the limb near the location of the blood flow measuring electrodes and amplifying the signal produced by the loop to produce a ballistic signal. This loop signal is then added, subtractively, to the combination of blood flow plus perturbation signal from the electrodes to substantially cancel out the undesired ballistic component.

15 Claims, 20 Drawing Figures

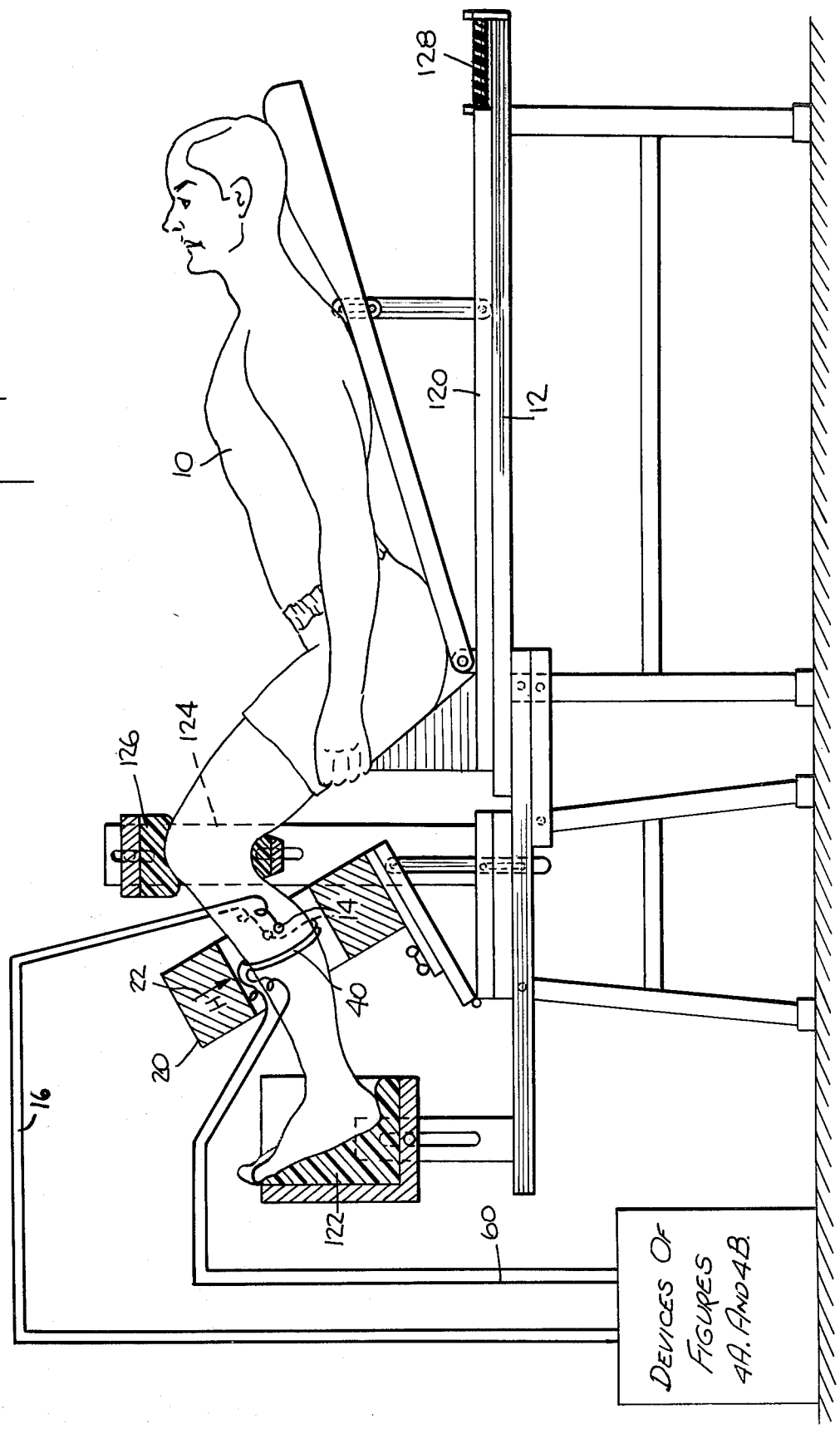

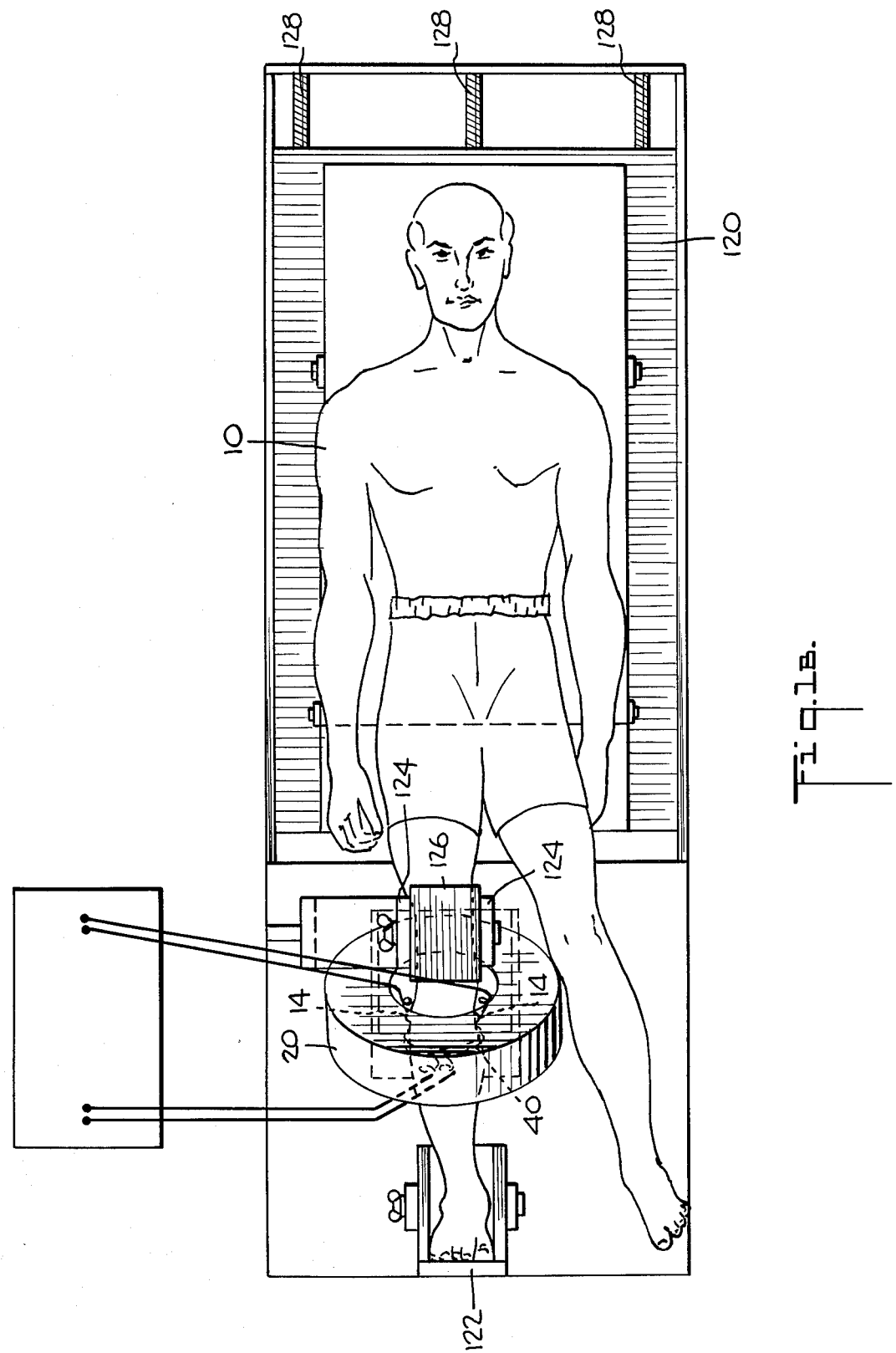

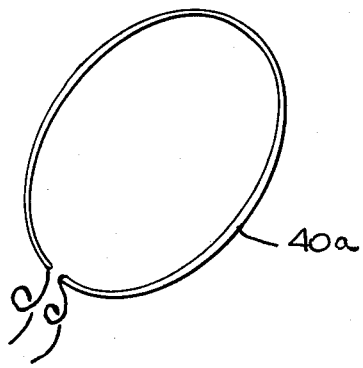
Fig.2.
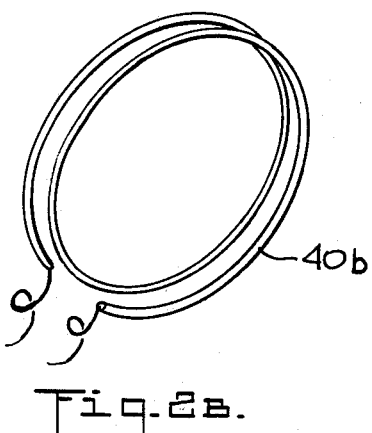
Fig.2A.
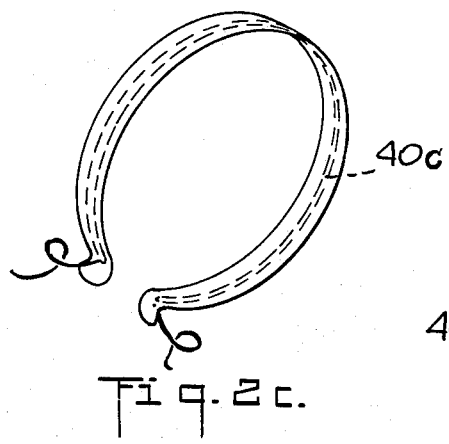
Fig.2B.
Fig.2C.
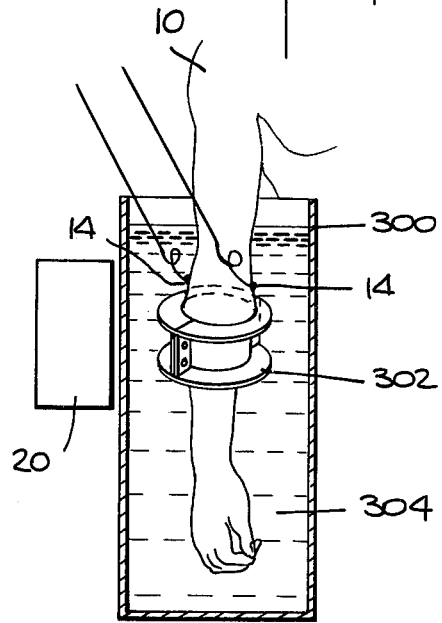
Fig.3.
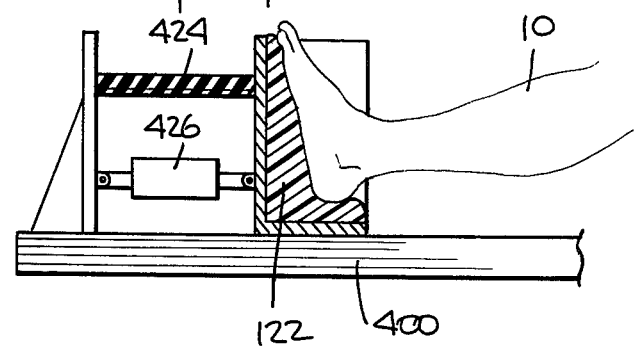
Fig.3A.
Fig.3B.
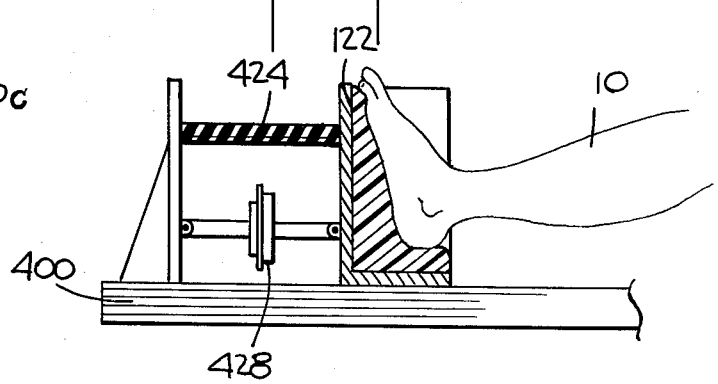
Fig.3C.

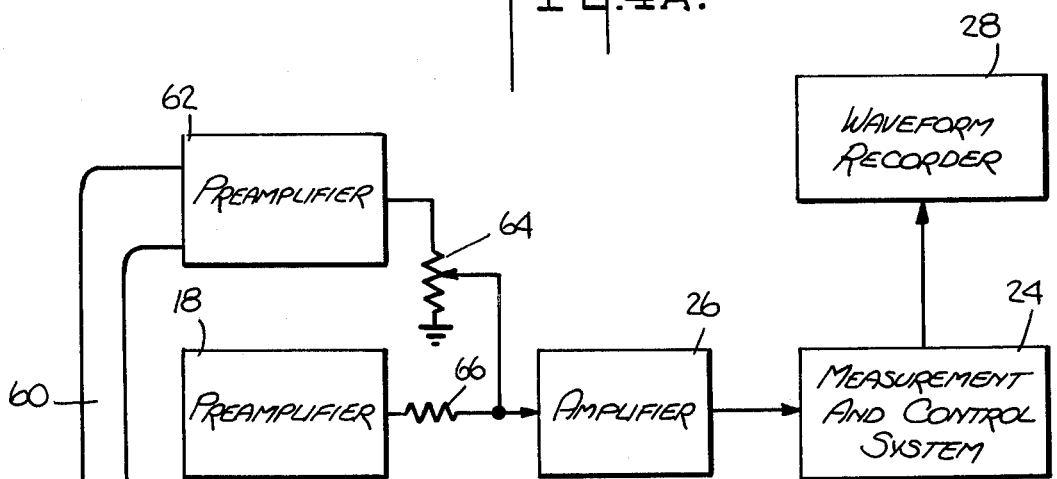
Fig.4A.
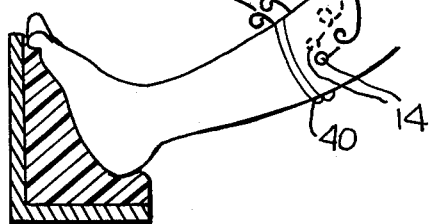
Fig.4.
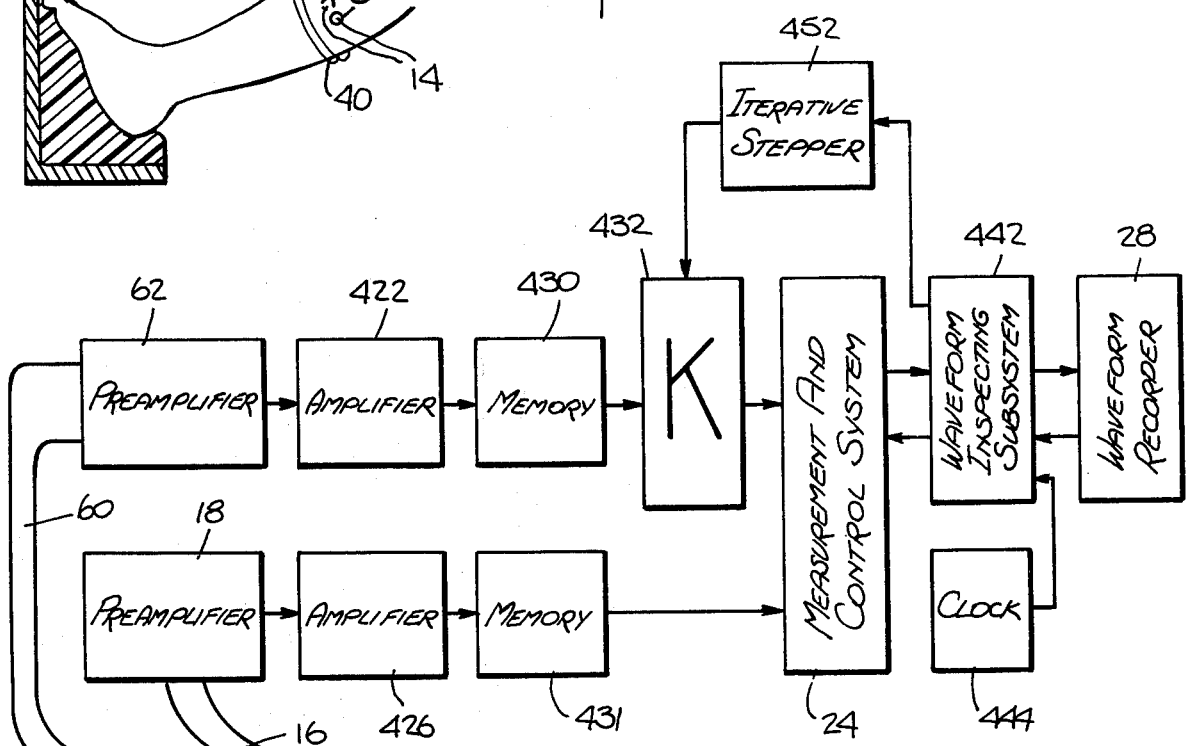
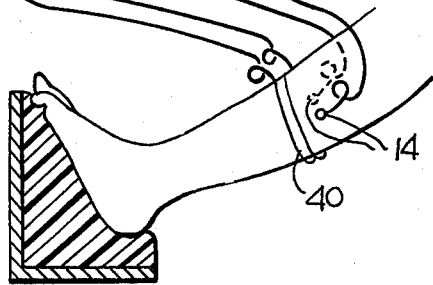
Fig.4B.

Total Signal
(Blood Flow + Artifact)

Normal Subject

"Waveforms Without Correction"

Total Signal
(Blood Flow + Artifact)

Sick Subject

"Lower Calf"

Blood Flow Signal +
Ballistic Perturbation

Ballistic Artifact

"Clean Blood Flow"

Total Signal

Artifact Captured By Loop

APPARATUS AND METHOD FOR ELIMINATING PERTURBATIONS OF A KINETIC ORIGIN IN THE BLOOD FLOW WAVEFORM

BACKGROUND OF THE INVENTION

The present invention relates to blood flow measurements and particularly to the elimination of perturbations in the blood flow waveform caused by mechanical movements of the body.

It is known that the strong ejection of blood from the ventricle of the heart into the arch of the aorta creates a transfer of mass because of the blood movement. This mechanically shifts the center of gravity of the body, which in turn creates reaction forces which act upon the body. As a result, a small bodily displacement or recoil is created which is synchronous with the ejection of the blood. These bodily displacements are recorded by ballistocardiographs, which display ballistocardiograms showing the movement of the totality of the body.

One type of ballistocardiographic apparatus is disclosed in U.S. Pat. No. 2,684,671 issued on July 27, 1954 to S. Mendelsohn wherein a displacement ballistocardiogram is recorded by photoelectric or electromagnetic detection apparatus near the leg shins of the patient. The recordings are used to diagnose various conditions associated with malfunctioning of the heart and aorta.

It has been found that a heart synchronized ballistic artifact is present when making blood flow measurements on the limbs of a living being when a magnetic field is applied in the area of the limb for producing an electro-magnetic blood flow signal. The limb being a conductor, the movement causes induction of voltages within the limb. The amplitude of this ballistic perturbation is so significant in limb measurements that it distorts the true blood flow waveform. Also a part of the perturbation arrives during the quiescent part of the pulsatile blood flow waveform and thereby may affect the determination of the zero reference.

SUMMARY OF THE INVENTION

It is an object of the present invention to provide a method and apparatus for eliminating or minimizing the perturbations of the blood flow waveform caused by mechanical movements of the body, such as the body recoil due to the systolic blood ejection herein referred to as "ballistic artifact." This and other objects are achieved by the present invention which provides an apparatus and method of cancelling the ballistic electric perturbation of the blood flow waveform which comprises the placement of a loop of electrically conductive wire around the limb and in proximity to the electrodes which collect the blood flow signal. The pulsatile blood flow signal can be measured by the systems disclosed in U.S. Pat. Nos. 3,659,591; 3,759,247; and 3,809,070 or by other conventional methods. One or more turns of wire form the rigid loop which is coaxial with and attached to the limb. In operation, the movement of the limb, caused by the ballistic influence of the heart, induces an electrical signal in the loop which is passed on to one of the amplifiers in the measuring system. The wires in the loop are connected to an amplifier, the output of which is connected to adjustment means for adjusting the level of the voltage originating at the loop in proportion with the voltage measured through the blood flow electrodes, and associated amplifier. This induced loop signal is electrically substracted from the perturbated blood flow signal picked up by the electrodes and electrode connections, and the resultant signal is utilized by the system. Since the overall blood flow signal includes the ballistic perturbation before the subtraction, then the effect of the induced loop signal is to substantially cancel the perturbation portion from the overall blood flow signal.

The apparatus further includes a footrest which firmly holds the heel. Also, there is included knee support which restrains the knee laterally and therefore allows the knee to move in one direction only, leaving only 1° of freedom and channelling the kinetic energy towards one single motion.

Also included is a means for applying pressure along the leg to insure that the heel holds tightly against the heel rest. This means can comprise a mechanical force, such as a weight pulling the sliding support of the hips and buttocks toward the heel. Also included is a means for applying elastic pressure on the knee-cap, downwards, to insure that the heel holds firmly against its heel rest. Furthermore, there may be provided devices which momentarily oppose vibratory displacements, either by viscosity due to a viscous liquid in which parts of the limb is immersed, by a hydraulic shock absorber by a pneumatic dash-pot, or by a combination thereof, all of which have the ability to allow a slow positioning of the limb, but restrain any rapid movement. The method described herein channels the kinetic energy towards one major direction of motion, preferably rotational in a vertical plane with the ankle being the fixed chamber of rotation. The method utilizes an optimal positioning of the limb, bent at an angle from the horizontal, such as an angle of 30°.

Thus, the method and apparatus permit the isolation and recording of the local ballistogram and those muscular tremors which are repetitive vibrations triggered by the heart contraction. The measuring system subtracts the signal captured by a loop, from the signal captured by the electrodes and the electrode connections. Such signals are due to the blood flow and the limb motion caused by the kinetic artifact.

BRIEF DESCRIPTION OF THE DRAWINGS

FIGS. 1A and 1B are schematic drawings of the mechanical arrangement holding the patient's leg, illustrative of the present invention;

FIGS. 2A, 2B and 2C are detailed drawings of loop arrangements and attachment means therefor;

FIGS. 3A, 3B and 3C illustrate alternate mechanical means for dampening the motion of the limb;

FIGS. 4A and 4B are schematic electrical diagrams of the device used with blood flow measurements, illustrative of the present invention;

FIG. 5A is a blood flow waveform of a normal subject wherein the curve includes a perturbation preceding the main blood flow signal taken with the device shown in FIG. 1A, without cancellation;

FIG. 5B is a blood flow waveform of a sick person taken with the device shown in FIG. 1A, without cancellation, wherein the perturbation is so strong that the main blood flow waveform is difficult to recognize;

DESCRIPTION OF THE PREFERRED EMBODIMENTS

Figure 6A:
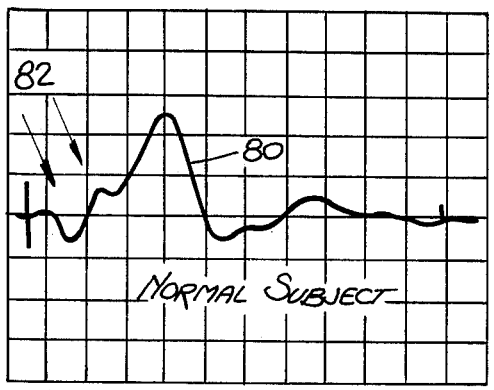
FIGS. 6A and 6B are curves taken on a normal subject to illustrate that the perturbation is of a ballistic or mechanical nature, with FIG. 6A showing the total blood flow waveform including any effects of the ballistic artifact, and FIG. 6B showing the ballistic waveform captured by the loop placed around the calf, with the first half of each of the waveforms of FIGS. 6A and 6B being taken with the subject in a supine position while the last half of such waveforms is taken with the subject in a sitting position.

FIGS. 1A and 1B show a subject 10 lying on an examining table 12. The mattress is on a sliding support 120. A force is applied to the sliding support 120 to push it towards the heel of the subject. The force may comprise a spring 128. The knee is laterally positioned by side baffles 124. The knee is pressed downwards by a knee rest 126 having a soft pad. The heel is firmly held by a heel rest 122. A pair of electrodes 14 are attached to the calf of the subject for sensing the blood flow induced signals. Since it is desired to measure the blood flow through the calf, it is noted that a plurality of pairs of electrodes 14 can be employed for such measurement, such as is disclosed in applicant's co-pending U.S. application Ser. No. 533,528, filed on Dec. 17, 1974 and entitled Revolving Symmetrical Magnet Assembly And Improved Method Of Blood Flow Detection.

A permanent magnet 20 is located at the level of the electrodes 14 and provides a homogeneous magnetic field 22 in the region of the calf under study. The strength of this magnetic field is sufficient so that a detectable electric signal, induced by the passage of blood through the magnetic field in the artery under study, is present at the skin surface of the leg where the electrodes 14 are attached. The apparatus and method for making blood flow measurements using non-invasive electrodes and a stable and homogeneous magnetic field is disclosed in U.S. Pat. Nos. 3,659,591, 3,759,247 and 3,809,070, issued to Henri G. Doll and Hans J. Broner.

A loop 40 is attached to the calf near the electrodes. The mechanical body recoil due to the surge of blood upon each heart cycle, such as studied by ballistocardiography causes also a movement of the leg. This movement of the leg due to the ballistic impulse, manifests itself initially as a downward movement of the bone and consequently the flesh and finally the skin. This movement is detected by the loop 40 attached to the skin since there is a relative movement with respect to the magnetic field. Loop 40 is connected by wires 60 to the electrical system shown in FIGS. 4A or 4B. Since the leg becomes a moving conductor in the magnetic field 22, a voltage is induced in the electrodes 14. Electrodes 14 are connected by wires 16 to the electrical system shown in FIGS. 4A or 4B.

FIG. 2A represents a loop 40a comprised of a rigid coil of one turn of electrically conductive wire which is to be positioned coaxially around the calf in proximity to the electrodes 14. The loop 40a picks up a sufficient induced voltage when the calf is moved and displaces the loop. In one embodiment, the loop 40a may comprise a single turn of No. 18 wire having the same diameter as the calf. This single turn of wire fits around the calf and can be secured to the calf by means of tape attached to the skin.

FIG. 2B represents a loop 40b made of more than one turn of wire. The loop is attached around the leg by means of tape or otherwise. In a further embodiment shown in FIG. 2C the loop 40c is a C-shaped spring clamp which grabs on to the calf. The diameter of this elastic clamp may, for example, be 4 inches.

FIGS. 3A, 3B and 3C represent alternate restraining devices to firmly maintain the limb by dampening fast ballistic motions. FIG. 3A represents a solution which utilizes a viscous liquid 304 in a container 300. A system of fins 302 is clamped to the limb. The magnet 20 and electrodes 14 are also shown. FIG. 3B represents a system which applies pressure to the heel by a spring 424 pushing the foot rest 122. A hydraulic shock absorber 426 dampens the displacement of the heel. FIG. 3C represents a similar solution where a pneumatic dashpot 428 dampens the displacement of the heel.

FIGS. 4A and 4B show the electrical system for processing the voltages originating from the patient to obtain the best cancellation of the perturbation. The induced voltage signal in the loop 40 is applied via lines 60 to an amplifier 62. The polarities of the connections are chosen such that the signals from an amplifier 18 and amplifier 62 are added subtractively in the final output of the flowmeter. More particularly, FIG. 4A represents one implementation of the method by simultaneous subtraction of the artifact signal. Here, the differential amplifiers 18 and 62 amplify, respectively, the total blood flow and other signals appearing between the measuring electrodes 14 and the ballistic signals picked up by the loop 40. A variable resistor 64 is connected at the output of amplifier 62 and determines the amplitude coefficient K-1 needed to match the amplitude of the artifact signal picked up by the loop 40, with the amplitude of the perturbating ballistic component superimposed on the blood flow waveform picked up by the electrodes 14. Thus, the criterion used for adjusting the value of the resistor 64 is the ratio of the loop signal to the blood flow electrode signal, chosen such that any induced voltage produced during the "quiescent period" is cancelled. A resistor 66 is connected at the output of the differential amplifier 18. The other sides of the variable resistor 64 and the resistor 66 are connected to the input of amplifier 26 which essentially subtracts the loop signal from the electrode signal. Alternatively, amplifier 26 may comprise a differential amplifier with its two inputs connected respectively to the resistors 64 and 66.

A measurement and control system 24 is provided which is basically similar to the systems disclosed in the above-noted patents. System 24 receives an input from an amplifier 26 which is connected to the output of the differential amplifier 18. The measurement and control system 24 includes appropriate filter circuits, a waveform averaging circuit for accumulating blood flow waveforms, a counter circuit connected to the waveform averaging circuit which is advanced by one step in synchronism with each blood flow waveform signal, and a synchronization circuit which provides trigger pulses for the counter circuit is response to sensed electrocardiogram signals. A control circuit receives signal from the counter circuit and in turn controls the number of cycles entered into the waveform averaging circuit. A waveform recorder 28 is connected to the measurement and control system 24 for displaying the blood flow waveform derived in the waveform averaging circuit of such system 24.

The effect of the polarity of the inputs to the amplifiers 18 and 62 and the combining of the outputs of these amplifiers is to substantially cancel the perturbations portion of the overall signal which also contains blood flow, resulting in a substantially pure blood flow signal. This resultant artifact-free sequence of blood flow signals are passed from the amplifier 26 to the measurement and control system 24 which accumulates a predetermined number of cycles in the waveform averager and selectively displays the blood flow as a waveform on the recorder 28.

FIG. 4B represents an alternate implementation by sequential subtraction. Amplifiers 422 and 426 include analogue to digital converters and are connected to pre-amplifiers 62 and 18, respectively. The output of the amplifiers 18, 426, 62 and 422 are fed to a computer, and processed individually in a manner generally similar to that described in U.S. Pat. No. 3,659,591. The sequence of signals representing the ballistic artifact are averaged in a waveform averager and stored in a memory 430 connected to amplifier 422. The contaminated waveform which contains the blood flow and the perturbation due to the ballisic artifact is also averaged in waveform and stored in another memory 431 connected to amplifier 426. These memories therefore store the smoothed and heart-synchronized parts of the signals originating respectively at the electrodes 14 and the loop 40.

First, the waveform, representing, and local ballistogram, all kinetic artifacts synchronous with the heart, is displayed for visual inspection, Second, the amplitude of this ballistic waveform is modified by the divider 432 with a ratio K. This ratio K is controlled by a sequential stepper 452. The output of the divider 432 and the output of the memory 431 are subtractively combined in the measurement and control system 24. Initially, the coefficient K applied by divider 432 is small. The resultant waveform represents the blood flow, unchanged, and a modified perturbation related to the ballistic artifact. This waveform is examined by the waveform inspecting subsystem 442. This waveform inspecting subsystem 442 monitors the part of the resulting subtractive output, which represents the time span from the R synchronization to about 0.15 seconds thereafter. This span of time is defined by the clock 444 connected to subsystem 442. If the voltages during this span of time vary more than a preset value, as sensed by the inspecting subsystem 442, then the stepper 452 causes the ratio setting system 32 to increase the ratio K by about 10% and the new combination waveform is subtractively generated by again taking stored waveforms from the memories 430 and 431. This operation repeats itself by iterative steps, with progressive increases of the coefficient K. At some step, the inspection of the resultant waveform satisfies the criterion, which is that, during the 0.15 second span of time considered, the voltages do not vary appreciably. This corresponds physiologically to the "quiescent" state, prior to the arrival of the systolic blood ejection at the level of the calf. At that step, the waveform inspecting subsystem allow the waveform recorder 28 to trace the resulting curve, which represents the blood flow waveform, with a minimized perturbation due to the ballistic artifact.

FIG. 5A shows a blood flow waveform 80 of a normal subject wherein the waveform 80 includes the ballistic perturbation preceding the main blood flow waveform, as indicated by arrows 82. The waveform 80 shown in FIG. 5A represents the signal picked up by electrodes 14, prior to correction to remove the ballistic component.

FIG. 5B shows a blood flow waveform 86 of another person who is sick. Illustrated is the situation where the ballistic perturbation is so strong that the main blood flow waveform is difficult to distinguish. The waveforms 80 and 86 were both taken by electrodes 14 attached to the lower calf.

Figure 6B:
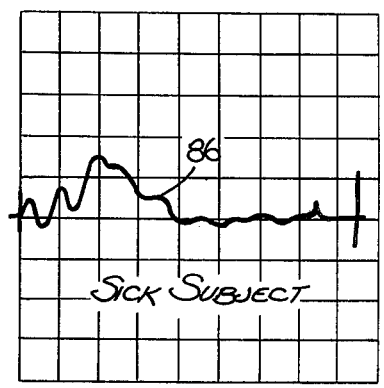

The FIGS. 6A and 6B are provied to illustrate the ballistic or mechanical nature of the artifact. FIG. 6A includes a blood flow waveform 90A taken when the subject is in a supine position, while the waveform portion 90B was taken with the same subject in a sitting position. Waveforms 90A and 90B are separated by a time span indicated by line 92. Both of the waveforms 90A and 90B were taken at the electrodes 14 with the electric and magnetic conditions essentially the same. It can be observed that in the sitting position, the recoil effect is absorbed into the mattress of the table 12 without shaking the limb, therefore, the ballistic perturbation is relatively insignificant in the waveform portion 90B.

In FIG. 6B, the waveforms 94A and 94B were taken of the signal generated at the loop 40 with the subject respectively in the supine position and the sitting position. Waveforms 94A and 94B are separated by a time span indicated by line 96. It can be seen that the ballistic signal 94A captured by the loop 40 is recognizable with the subject is in the supine position whereas the waveform 94B shows essentially no pick-up at the loop 40 when the subject is sitting. It is noted that the blood flow waveforms shown in FIG. 6A and the loop signals shown in FIG. 6B were taken for a healthy subject under essentially the same electrical conditions.

Figure 7A:
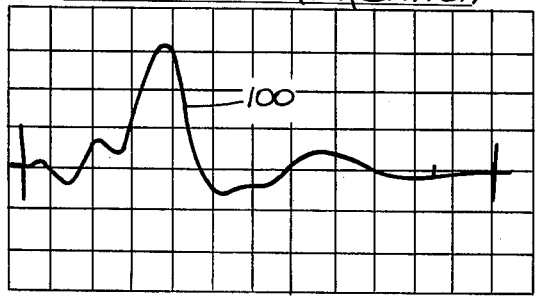
FIGS. 7A, 7B and 7C are curves illustrating the correction of the perturbation due to the ballistic displacement, with FIG. 7A showing a perturbated waveform, FIG. 7B showing the signal induced in the loop attached to the limb, and FIG. 7C showing the resultant blood flow curve after the ballistic loop voltage shown in FIG. 7B has been subtracted from the uncorrected blood flow voltages shown in FIG. 7A.
Figure 7B:
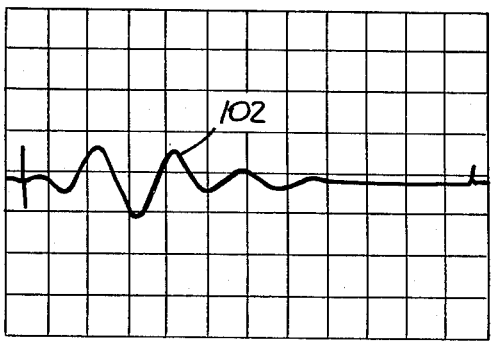
Figure 7C:
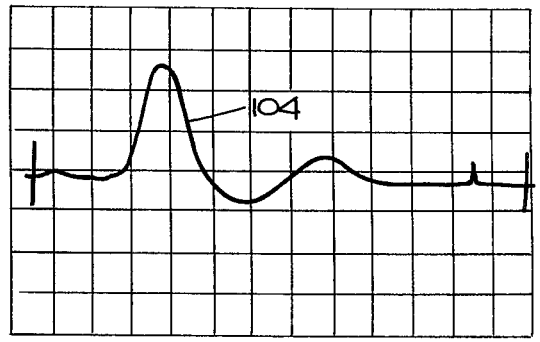
Figure 6A:
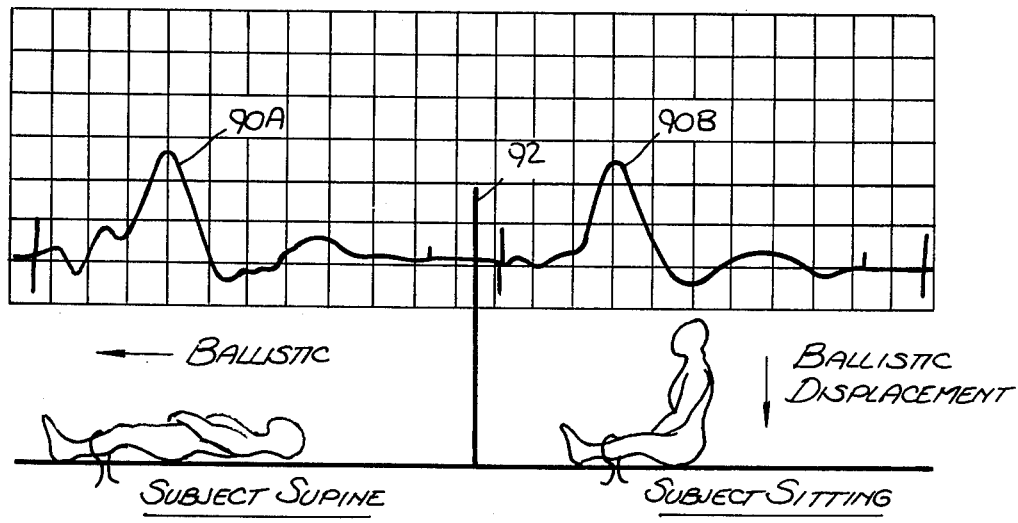
Figure 6B:
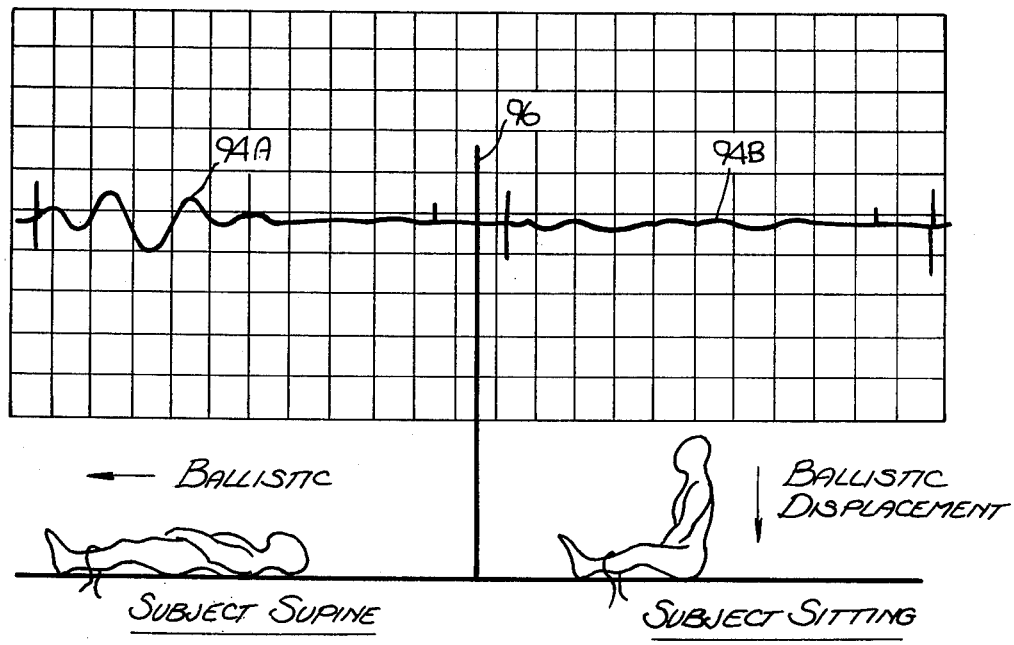

The FIGS. 7A, 7B and 7C illustrate the correction of the ballistic perturbation in the blood flow signal. In FIG. 7A, a blood flow waveform 100 produced at electrodes 14 is shown and includes the combined blood flow signal and the ballistic component picked up at the calf. FIG. 7B shows the ballistic waveform 102 picked up by the loop 40. The loop waveform 102 is shown after adjusting the resistor 64 shown in FIG. 7A to provide an amplitude which corresponds with the amplitude of the ballistic component of the blood flow waveform 100 shown in FIG. 7A. FIG. 7C shows the resultant waveform 104 produced at the output of the amplifier 26 after the ballistic waveform 102 shown in FIG. 7B has been electrically subtracted from the overall blood flow signal 100 shown in FIG. 7A. The resultant blood flow waveform 104 is essentially free from the ballistic perturbation.

Although the above description is directed to the preferred embodiments of the invention, it is noted that other variations and modifications will be apparent to those skilled in the art, and, therefore, may be made without departing from the spirit and scope of the present disclosure.

What is claimed is:

1. An electromagnetic flowmeter apparatus for use in measuring the pulsatile flow in a blood vessel of a living subject, the flowmeter apparatus including means adapted to establish a uniform magnetic field in the vicinity of a limb of a living subject, electrode means adapted to be positioned within the magnetic field in conductive contact with said limb of a living subject for detecting electrical signals generated by pulsatile blood flow in the limb, and means coupled to the electrode means for producing a blood flow waveform from the signals detected by the electrode means, wherein the improvement comprises:

ballistic pickup means adapted to be positioned on the limb of the living subject in the magnetic field near the attachment location of the electrode means of said flowmeter for producing a signal in response only to movement of the limb and means having an input coupled to the ballistic pickup means and to the electrode means and an output coupled to the waveform producing means of the flowmeter for adding subtractively the ballistic signal produced by the ballistic pickup means to the electrical signals detected by the electrode means in such proportion as substantially to cancel an undesired ballistic component of a blood flow waveform produced by the waveform producing means of the flowmeter.

2. Apparatus as recited in claim 1 wherein said ballistic pickup means comprises:

an electrically conductive loop adapted to at least partially encircle the limb in close contact therewith and means connected to said loop for amplifying the signal produced by movement of the loop within the magnetic field in response to cardioballistic movement of the limb.

3. Apparatus as recited in claim 2 wherein said loop comprises at least one turn of wire.

4. Apparatus as recited in claim 1 and further comprising:

first amplifying means connected between the electrode means of the flowmeter and said adding means for amplifying the signals detected by said electode means;

second amplifying means connected between said ballistic pickup means and said adding means for amplifying the ballistic signals produced by said ballistic pickup means; and means for adjusting the relative amplitudes of the signals from said first and second amplifying means, such that the amplitude of the amplified ballistic signals entering the adding means from the second amplifying means is substantially the same as the ballistic component of the amplified signals entering the adding means from the first amplifying means, whereby subtractive addition of said signals by the adding means substantially eliminates the ballistic component in the blood flow waveform output of the flowmeter.

5. An electronic flowmeter apparatus for use in measuring the pulsatile flow in a blood vessel of a living subject, the flowmeter apparatus including means adapted to establish a magnetic field in the vicinity of a limb of a living subject, electrode means adapted to be positioned within the magnetic field in conductive contact with said limb of a living subject for detecting electrical signals generated by pulsatile blood flow in the limb, and means coupled to the electrode means for producing a blood flow waveform from the signals detected by the electrode means, wherein the improvement comprises:

ballistic pickup means adapted to be positioned on the limb of the living subject in the magnetic field near the attachment location of the electrode means of said flowmeter for producing a signal in response only to movement of the limb, said ballistic pickup means comprising an electrically conductive loop adapted to at least partially encircle the limb in close contact therewith, said loop comprising a C-shaped spring member which is adapted to clamp around said limb, and means connected to said limp for amplifying the signal produced by movement of the loop within the magnetic field in response to cardioballistic movement of the limb; and means having an input coupled to the ballistic pickup means and to the electrode means and an output coupled to the waveform producing means of the flowmeter for adding subtractively the ballistic signal produced by the ballistic pickup means to the electrical signals detected by the electrode means in such proportion as substantially to cancel an undesired ballistic component of a blood flow waveform produced by the waveform producing means of the flowmeter.

6. An electromagnetic flowmeter apparatus for use in measuring the pulsatile flow in a blood vessel of a living subject, the flowmeter apparatus including means adapted to establish a magnetic field in the vicinity of a limb of a living subject, electrode means adapted to be positioned within the magnetic field in conductive contact with said limb of a living subject for detecting electrical signals generated by pulsatile blood flow in the limb, and means coupled to the electrode means for producing a blood flow waveform from the signals detected by the electrode means, wherein the improvement comprises:

ballistic pickup means adapted to be positioned on the limb of the living subject in the magnetic field near the attachment location of the electrode means of said flowmeter for producing a signal in response only to movement of the limb;

means having an input coupled to the ballistic pickup means and to the electrode means and an output coupled to the waveform producing means of the flowmeter for adding subtractively the ballistic signal produced by the ballistic pickup means to the electrical signals detected by the electrode means in such proportion as substantially to cancel an undesired ballistic component of a blood blow waveform produced by the waveform producing means of the flowmeter;

first amplifing means connected between the electrode means of the flowmeter and said adding means for amplifing the signals detected by said electrode means;

second amplifing means connected between said ballistic pickup means and said adding means for amplifying the ballistic signals produced by said ballistic pickup means; and means for adjusting the relative amplitudes of the signals from said first and second amplifying means, such that the amplitude of the amplified ballistic signals entering the adding means from the second amplifying means is substantially the same as the ballistic component of the amplified signals entering the adding means from the first amplifying means, whereby subtractive addition of said signals by the adding means substantially eliminates the ballistic component in the blood flow waveform output of the flowmeter, and wherein said means for adjusting the relative amplitudes of the signals from the first and second amplifying means comprises means for sampling the output of the adding means during the quiescent periods of the pulsatile blood flow cycles and means connected between the sampling means and the input to the adding means from the second amplifying means for adjusting the amplitude of the input from the second amplifying means to the adding means such that the amplitude of the sampled output during the quiescent periods is less than a predetermined value.

7. Apparatus as recited in claim 6 and further comprising memory means connected between the outputs of said first and second amplifying means and the inputs of said adding means for storing the signals amplified in said amplifying means.

8. Apparatus as recited in claim 7 wherein said memory means include first means for averaging, in waveform, the amplified signals from said ballistic pickup means and second means for averaging, in waveform, the amplified signals from the electrode means, said waveform averaged signals being combined in said adding means.

9. An electromagnetic flowmeter apparatus for use in measuring the pulsatile flow in a blood vessel of a living subject, the flowmeter apparatus including means adapted to establish a magnetic field in the vicinity of a leg of a supine human being for detecting electrical signals generated by pulsatile blood flow in the leg, and means coupled to the electrode means for producing a blood flow waveform the signals detected by the electrode means, wherein the improvement comprises:

a fixed heel rest adapted to receive the heel of a leg of a human subject for restraining axial movement of the lower leg in the direction of said heel rest;

ballistic pickup means adapted to be positioned on said leg near the location of said electrode means of the flowmeter for producing a ballistic signal in response to cardioballistic movement of the leg; and means having an input coupled to the ballistic means and to the electrode means and an output coupled to the blood flow waveform producing means of the flowmeter for adding subtractively the ballistic signal produced by the ballistic pickup means to the electrical signals detected by the electrode means in such proportion as substantially to cancel an undesired ballistic component of the blood flow waveform output of the flowmeter.

10. Apparatus as recited in claim 9 wherein said apparatus further comprises a pair of side baffle supports adapted to be positioned in space relation to said heel rest on each side of the knee of the leg being examined for restraining the leg against lateral movement while permitting movement in a single plane including the upper and lower leg.

11. Apparatus as recited in claim 10 wherein said apparatus further comprises a knee rest mounted between the side baffle supports and having a soft pad adapted to press downward on the top of the knee of the leg being examined when the leg is bent so that the lower leg makes a predetermined angle with the horizontal, thereby to urge the heel of the leg into firm contact with the heel rest.

12. An electromagnetic flowmeter apparatus for use in measuring the pulsatile flow in a blood vessel of a living subject, the flowmeter apparatus including means adapted to establish a magnetic field in the vicinity of a leg of a supine human being, electrode means adapted to be positioned within the magnetic field in conductive contact with said leg of a human being for detecting electrical signals generated by pulsatile blood flow in the leg, and means coupled to the electrode means for producing a blood flow waveform from the signals detected by the electrode means, wherein the improvement comprises:

a support member adapted to support the buttocks and back of a supine human subject, whose leg blood flow is being examined, said support member being reciprocally slidable in a substantially horizontal direction generally aligned with the body of the human subject;

ballistic pickup means adapted to be positioned on said leg near the location of said electrode means of the flowmeter for producing a ballistic signal in response to cardioballistic movement of the leg; and means having an input coupled to the ballistic pickup means and to the electrode means and an output coupled to said waveform producing means of the flowmeter for adding subtractively with ballistic signal produced by the ballistic pickup means to the electrical signals detected by the electrode means in such proportion as substantially to cancel an undesired ballistic component of the blood flow waveform output of the flowmeter.

13. Apparatus as recited in claim 12 wherein the apparatus further comprises resilient means for urging said slidable support in the direction of the heel of the leg being examined.

14. Apparatus as recited in claim 13 wherein the apparatus further comprises a fixed heel rest spaced generally horizontally from the end of the slidable support member adapted to support the buttocks of a supine human subject and adapted to receive the heel of the leg being examined so as to restrain axial movement of the lower leg in the direction of said heel rest, the range of slidability of said support member with respect to said heel rest being sufficient to allow the lower portion of the leg being examined to assume a predetermined angle with respect to the horizontal.

15. Apparatus as recited in claim 14 wherein said apparatus further comprises a pair of side baffle supports adapted to be positioned in spaced relation to said heel rest on each side of the knee of the leg being examined so as to restrain the leg against lateral movement while allowing movement in a single plane including the upper and lower portions of the leg.

* * * * *

UNITED STATES PATENT OFFICE
CERTIFICATE OF CORRECTION

Patent No. 4,036,215　　　　　　　　Dated July 19, 1977

Inventor(s) Henri Georges Doll　　　　　　Page 1 of 2

It is certified that error appears in the above-identified patent and that said Letters Patent are hereby corrected as shown below:

| | |
|---|---|
| In the Title: | after "Apparatus" delete "And Method". |
| Column 2, line 23: | change "parts" to --part--. |
| Column 2, line 31: | change "chamber" to --center--. |
| Column 4, line 61: | change "is" to --in--. |
| Column 4, line 62: | change "signal" to --signals--. |
| Column 5, line 3: | change "perturbations" to --perturbation--. |
| Column 5, line 28: | change "and" to --as--. |
| Column 5, line 31: | after "inspection" change "," to --.--. |
| Column 5, line 49: | change "32" to --432--. |
| Column 6, line 28: | change "with" to --when--. |
| Column 7, line 34: | change "electode" to --electrode--. |

UNITED STATES PATENT OFFICE
CERTIFICATE OF CORRECTION

Patent No. 4,036,215　　　　　　　　　Dated July 19, 1977

Inventor(s)　Henri Georges Doll　　　　Page 2 of 2

It is certified that error appears in the above-identified patent and that said Letters Patent are hereby corrected as shown below:

Column 8, line  3:　change "limp" to --loop--.

Column 8, line 39:　change "blow" to --flow--.

Signed and Sealed this

Twenty-fifth Day of October 1977

[SEAL]

Attest:

RUTH C. MASON　　　　　　　LUTRELLE F. PARKER
Attesting Officer　　　Acting Commissioner of Patents and Trademarks